US011612699B2

(12) United States Patent
Helmer

(10) Patent No.: US 11,612,699 B2
(45) Date of Patent: Mar. 28, 2023

(54) INJECTION DEVICE WITH A REMOTE CONTROL

(71) Applicant: SANOFI, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 188 days.

(21) Appl. No.: 16/771,084

(22) PCT Filed: Dec. 17, 2018

(86) PCT No.: PCT/EP2018/085111
§ 371 (c)(1),
(2) Date: Jun. 9, 2020

(87) PCT Pub. No.: WO2019/121447
PCT Pub. Date: Jun. 27, 2019

(65) Prior Publication Data
US 2021/0187204 A1      Jun. 24, 2021

(30) Foreign Application Priority Data

Dec. 18, 2017   (EP) ..................................... 17306802

(51) Int. Cl.
*A61M 5/315*       (2006.01)
(52) U.S. Cl.
CPC ...... *A61M 5/31576* (2013.01); *A61M 5/3157* (2013.01); *A61M 2005/31588* (2013.01);
(Continued)
(58) Field of Classification Search
CPC .... A61M 5/31576; A61M 2005/31588; A61M 2209/01
See application file for complete search history.

(56) References Cited

U.S. PATENT DOCUMENTS 9,125,991 B2 *   9/2015  Schabbach ........... A61B 5/4839
2004/0024364 A1  2/2004  Langley et al.
(Continued)

FOREIGN PATENT DOCUMENTS

CN    104203315    12/2014
CN    105228672    1/2016
(Continued)

OTHER PUBLICATIONS

PCT International Preliminary Report on Patentability in International Appln. No. PCT/EP2018/085111, dated Jun. 23, 2020, 8 pages.

(Continued)

*Primary Examiner* — Amber R Stiles
*Assistant Examiner* — Leah J Swanson
(74) *Attorney, Agent, or Firm* — Fish & Richardson P.C.

(57) ABSTRACT

In one aspect, the disclosure relates to an injection device configured for expelling of a dose of a medicament. The injection device comprises a housing configured to accommodate a medicament reservoir, and a drive mechanism comprising an electric propulsion configured to mechanically interact with the medicament reservoir and configured to withdraw or to expel an amount of the medicament from the medicament reservoir. The injection device has at least a first interface directly or indirectly connected to the electric propulsion and configured to connect to a second interface of an auxiliary electronic device. The electric propulsion is controllable by the auxiliary electronic device when the first interface and the second interface are interconnected.

20 Claims, 4 Drawing Sheets

(52) U.S. Cl.
CPC ............... *A61M 2205/3306* (2013.01); *A61M 2205/502* (2013.01); *A61M 2205/583* (2013.01); *A61M 2209/01* (2013.01)

(56) References Cited

U.S. PATENT DOCUMENTS

| | | | | |
|---|---|---|---|---|
| 2011/0118694 | A1* | 5/2011 | Yodfat | A61M 5/172 |
| | | | | 604/93.01 |
| 2015/0025503 | A1* | 1/2015 | Searle | G16H 20/13 |
| | | | | 604/67 |
| 2015/0328411 | A1* | 11/2015 | Friedman | A61M 5/008 |
| | | | | 604/198 |
| 2016/0106927 | A1* | 4/2016 | Moeller | A61M 5/20 |
| | | | | 604/152 |
| 2017/0274149 | A1* | 9/2017 | Aeschlimann | H04Q 9/00 |
| 2017/0286638 | A1 | 10/2017 | Searle et al. | |
| 2017/0316158 | A1 | 11/2017 | Klemm et al. | |

FOREIGN PATENT DOCUMENTS

| | | |
|---|---|---|
| JP | 2013-521963 | 6/2013 |
| JP | 2017-500907 | 1/2017 |
| WO | WO 2011/117212 | 9/2011 |
| WO | WO 2013/120778 | 8/2013 |
| WO | WO 2014/181355 | 12/2014 |
| WO | WO 2015/066522 | 5/2015 |
| WO | WO 2017/032590 | 3/2017 |

OTHER PUBLICATIONS

PCT International Search Report and Written Opinion in International Appln. No. PCT/EP2018/085111, dated Feb. 1, 2019, 11 pages.

\* cited by examiner

INJECTION DEVICE WITH A REMOTE CONTROL

CROSS-REFERENCE TO RELATED APPLICATIONS

The present application is the national stage entry of International Patent Application No. PCT/EP2018/085111 filed on Dec. 17, 2018, and claims priority to Application No. EP 17306802.4, filed on Dec. 18, 2017, the disclosures of which are incorporated herein by reference.

TECHNICAL FIELD

The present disclosure relates to an injection device configured for expelling of a dose of a medicament and to an auxiliary electronic device configured for coupling to such an injection device. In another aspect the disclosure relates to an injection system comprising an injection device and comprising an auxiliary electronic device coupled to the injection device. In a further aspect the disclosure relates to a computer program with computer-readable instructions to be executed by a processor of an auxiliary electronic device configured for coupling to an injection device.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and scarhould be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod to operably engage with a bung or piston of the cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been dispensed or used-up.

With some drug delivery devices, such as pen-type injection devices a user has to set a dose of variable size by rotating a dose dial and a dose dial sleeve in a clockwise or dose-incrementing direction relative to a body or housing of the injection device. For injecting and expelling of a dose of a liquid medicament the user will have to depress a trigger or dose button in a distal direction and hence towards the body or housing of the injection device. Typically, the user uses his thumb for exerting a distally directed pressure onto the dose button, which is located at a proximal end of the dose dial and the dose dial sleeve, while holding the housing of the injection device with the remaining fingers of the same hand.

There exist injection devices, such as pen-type injectors that are configured as disposable devices. They are pre-filled with an injectable medicament. When the medicament is used up the entire injection device it is intended to be discarded. There exist also reusable injection devices that are equipped with a medicament container or medicament reservoir which is intended to be exchanged once the medicament contained therein has been used up. Such reusable injection devices enable a replacement of a medicament reservoir or medicament container, such as a cartridge.

For injection devices it is desirable to enable a precise, reliable and quasi automated supervising and/or collection of injection-related data during use of the injection device. Such injection devices may be equipped with an electronically implemented add-on device or data collection device configured to monitor user-induced operation of the injection device. A data collection device for attachment to an injection device should be rather compact with regards to its geometric size. For data collection devices configured for attachment to mechanically implemented injection devices it is a challenge to detect and/or to quantitatively measure the manual operation of the device conducted by the user of the device, e.g. when a user rotates a dial member of the injection device during setting of a dose or when a rotatable component of the injection device is subject to rotation during expelling of a dose. But also with electronically implemented injection devices it is desirable to provide a precise, reliable and failure safe quantitative measuring of rotatable components of the injection device.

With both types of injection device it is desirable to monitor operation of the injection device, e.g. in terms of monitoring the size of a dose injected, the time, when a dose has been injected and other injection related parameters.

SUMMARY

The present disclosure provides an injection device, an auxiliary electronic device for coupling to an injection device and an injection system comprising an injection device and comprising such an auxiliary electronic device that enables a universal coupling. The auxiliary electronic device, when coupled or engaged with the injection device should provide advanced functions that extend beyond a mere monitoring of an operation of the injection device. Moreover, the injection device should comprise a rather simple structure. The costs for manufacturing the injection device should be at a moderate or rather low level. The injection device should comprise a compact design and a compact geometry. The auxiliary electronic device should be connectable or should be configured for coupling to a variety of different injection devices, provided that the injection devices and the auxiliary electronic device comprise mutually matching interfaces.

In one aspect there is provided an injection device configured for expelling of a dose of a medicament. The injection device comprises a housing configured to accommodate a medicament reservoir. The injection device further comprises a drive mechanism. The drive mechanism comprises an electric propulsion or an electric drive configured to mechanically interact with the medicament reservoir. The drive mechanism and the electric propulsion are configured to withdraw or to expel an amount of the medicament from the medicament reservoir, i.e. they should be configured to withdraw or to expel a dose of the medicament of a predefined or of variable, user-defined size.

The injection device further comprises a first interface directly or indirectly connected to the electric propulsion. The first interface is configured to connect to a second interface of an auxiliary electronic device. The electric propulsion is controllable by the auxiliary electronic device when the first interface and the second interface are interconnected. The auxiliary electronic device is a separate device. It does not coincide with the injection device and differs from the injection device. The auxiliary electronic device typically comprises a user interface and a processor in order to control the electric propulsion of the injection device when the auxiliary electronic device and the injection device are mutually coupled through the mutually interconnected first and second interfaces. In this way the injection device does not require an own processor or a respective electronic control circuit. Operation of the drive mechanism may be entirely governed by the auxiliary electronic device. Without a connection of the auxiliary electronic device with the injection device the injection device could be inoperable. In this way, the injection device could not operate stand alone, without a coupling to the auxiliary electronic device.

The auxiliary electronic device typically comprises a memory and a communication interface connected to the processor of the auxiliary electronic device. In this way, the auxiliary electronic device and its electronic components are configured to monitor operation of the injection device. The auxiliary electronic device is configured at least to record a dosing history of the injection device. The auxiliary electronic device is configured to keep track of at least one of the number of doses, the size of the doses and the points of time, when respective doses have been set and expelled or injected.

In that the auxiliary electronic device is configured to control an electric propulsion of the injection device and in that the injection device may be void of an own electronic control circuit it is mandatory to establish a coupling or a connection between the injection device and the auxiliary electronic device for setting and/or dispensing of a dose of the medicament. In this way it is somehow guaranteed, that every dispensing or expelling action of the injection device can be and will be monitored by the auxiliary electronic device.

Since the injection device comprises an electric propulsion controllable by the auxiliary electronic device no further sensors are required for the auxiliary electronic device in order to measure or to detect a size of a dose actually set or expelled by the injection device. By controlling the electric propulsion and by controlling the drive mechanism through the auxiliary electronic device, the latter is inherently provided with information regarding the size of a dose actually dispensed and/or the remaining available units/volume of the medicament left in a drug container. Dose size information can be directly obtained from the electric control signals generated by the auxiliary electronic device and configured to control the electric propulsion of the injection device.

In a further example the first interface of the injection device comprises a first electric power connector configured to establish an electric power connection with a second electric power connector of the second interface. The second electric power connector belongs to the auxiliary electronic device. When the first electric power connector of the injection device and the second electric power connector of the auxiliary electronic device are interconnected electric power is transferable from the auxiliary electronic device to the injection device. Typically, the first electric power connector is directly or indirectly connected to the electric propulsion. Insofar, the injection device may be void of an own electric power source or power supply. The electric propulsion of the injection device may be powered by the auxiliary electronic device when the first electric power connector and the second electric power connector are interconnected. The electric propulsion of the injection device may be entirely powered by the auxiliary electronic device when the respective power connectors are interconnected.

The first electric power connector may be arranged in or at the first interface such that it automatically connects to the second electric power connector of the second interface when the first and the second interfaces are mutually interconnected. In this way, the first electric power connector and the second electric power connector do not require to become manually connected. The first and the second electric power connectors are arranged at the first interface and at the second interface, respectively, in such a way, that an electric power connection is established between the first and the second electric power connectors when the first and the second interfaces of the injection device and of the auxiliary electronic device are interconnected.

In some examples the injection device may comprise an own electric power source, such as a battery or such as a rechargeable battery. Here, the electric power connection provided by the first and the second electric power connectors may serve to recharge an onboard electric power source of the injection device. In this way, the injection device may also be equipped with an own electric power source of limited capacity that is rechargeable through an electric power connection with the auxiliary electronic device. The auxiliary electronic device may thus provide a charging functionality to the injection device.

According to a further example the first interface comprises a first data connector configured to establish a data connection with a second data connector of the second interface. The second data connector belongs to the auxiliary electronic device. When interconnected to the first data connector of the first interface of the injection device the second data connector is configured to transmit electric control signals to the electric propulsion. Insofar, the first data connector is directly or indirectly connected to the electric propulsion. Typically, electric control signals generated by the auxiliary electronic device and transferred to the injection device via the data connection are configured to trigger and/or to control an operation of the electric propulsion.

The data connection established by mutually interconnected first and second data connectors may comprise a bi-directional transmission of electronic data between the injection device and the auxiliary electronic device. The data connection between the injection device and the auxiliary electronic device enables a configuration of the injection device that is void of an own electronic control circuit. In this way, a processor or a respective electronic control circuit of the auxiliary electronic device can be directly connected to the electric propulsion of the injection device. The injection device may be thus void of an own electronic control circuit. In this way, manufacturing costs for the injection device can be decreased.

When the injection device is void of an own electronic control circuit the first data connector may be directly connected to the electric propulsion. In other examples the injection device may comprise an own electronic control circuit. Then, the first data connector is typically connected to the onboard electronic control circuit of the injection device. The electronic control circuit is then connected to the electric propulsion of the injection device. However, the electronic control circuit of the injection device may be controllable or configurable through the data connection with the auxiliary electronic device.

When the injection device is equipped with an own electronic control circuit the data connection established between the first and second data connectors may be of bi-directional type. Here, the first data connector of the injection device may be configured to receive electronic control signals as well as to transmit electronic control signals or electronic feedback signals to the auxiliary electronic device via the established data connection. In some examples the injection device may comprise an own electronic control circuit as well as an own electric power source. This enables at least a limited stand-alone operation of the injection device, e.g. for expelling at least a certain number of doses of the medicament. When establishing a data connection with the auxiliary electronic device, injection related data, such as size of a dose and a point of time when a respective dose has been set and/or expelled, can be transmitted to the auxiliary electronic device via the data connection.

The first data connector is located and arranged in or at the first interface of the injection device in such a way, that the data connection with the second data connector is automatically established when the first interface and the second interface are mutually interconnected.

In some examples the first electric power connector and the first data connector may coincide or may be implemented in a common plug or socket of the first interface. The same may be valid for the second electric power connector and the second data connector. Upon establishing an electric power connection by interconnecting the first electric power connector and the second electric power connector also a data connection is inherently established.

In a further example the injection device comprises a first mechanical connector configured to establish a mechanical connection with the auxiliary electronic device. The first mechanical connector may be configured to provide a form fitting mechanical interconnection to the auxiliary electronic device. For this, the housing of the injection device may comprise a male or female mechanical connector configured to mechanically and releasably engage with a correspondingly-shaped female or male connector of a housing of the auxiliary electronic device.

The first mechanical connector may be configured to releasably engage with a complementary or correspondingly-shaped second mechanical connector of the auxiliary electronic device. In other examples the first mechanical connector may be configured to mechanically engage with a housing of the auxiliary electronic device. Here, the first mechanical connector may be configured to receive a portion of a housing of the auxiliary electronic device. The auxiliary electronic device does not require any specific second mechanical connector in order to establish a mechanical connection with the injection device.

In some examples the first mechanical connector coincides with the first interface or includes the first interface of the injection device. In this way and upon establishing a mechanical connection between the injection device and the auxiliary electronic device the first and second interfaces of the injection device and the auxiliary electronic device may be inherently connected upon establishing a mechanical connection of the injection device with the auxiliary electronic device. For instance, a male or female plug or socket of the first interface may be located or integrated into the first mechanical connector in such a way that upon establishing a mechanical connection with the auxiliary electronic device a complementary or correspondingly-shaped male or female plug or socket of the injection device is connected to the respective plug or socket of the injection device. Typically, the first interface of the injection device comprises a plug and the second interface of the auxiliary electronic device comprises a socket configured to receive the plug of the injection device.

According to another example the injection device comprises a first optical interface configured to establish a light transmitting optical coupling with a second optical interface of the auxiliary electronic device. The first optical interface of the injection device may comprise a twofold function. The first optical interface may enable an optical or visual inspection of the content of the medicament reservoir and hence of the medicament. The first optical interface may further serve to provide a visual feedback to the user during use and operation of the injection device. By means of the light transmitting optical coupling to the second optical interface of the auxiliary electronic device the auxiliary electronic device becomes enabled to conduct a visual inspection of the content of the medicament reservoir.

In a further aspect the auxiliary electronic device may use the light transmitting optical coupling to illuminate at least a certain portion of the injection device when connected to the auxiliary electronic device. In this way the auxiliary electronic device may be configured to generate visual feedback signals that are discernible directly at the first optical interface or at other portions of the injection device. Insofar the light transmitting optical coupling between the injection device and the auxiliary electronic device provides visual inspection of the medicament reservoir and provides and enables illumination effects of the injection device. Since the first and second optical interfaces enable and establish a light transmitting optical coupling the injection device may be void of a light source.

A light source may be exclusively provided by the auxiliary electronic device. It is generally conceivable that the injection device comprises an own light source, e.g. in order to provide a visual optical feedback signal to the user, e.g. indicating that the injection device is ready for an injection procedure or that an injection procedure has terminated. Here, the optical coupling between the injection device and the auxiliary electronic device may be limited to a visual inspection of the content of the medicament reservoir. For instance, the first optical interface may overlap or may coincide with a window of a housing of the injection device. Through the window at least a portion of the medicament reservoir may be discernible and hence visually inspectable.

The second optical interface of the auxiliary electronic device may comprise a light source as well as a light detector, such as a camera. The second optical interface may be configured to visually inspect the integrity of the medicament located inside the medicament reservoir. For this, the second optical interface and hence the light source and the detector of the auxiliary electronic device may be configured to quantitatively measure an optical transmission or absorption coefficient of the medicament located in the medicament reservoir. A measurable absorption of the medicament may be indicative of the integrity of the medicament located in the medicament reservoir.

In another example the injection device is void of at least one of an electronic control circuit, an electric power source and a light source. The injection device may be void of at least two of the above mentioned components, electronic control circuit, electric power source and light source. The injection device may be void of an electronic control circuit, an electric power source and a light source. In this way manufacturing costs and respective expenditures can be further decreased. In other examples the injection device may comprise at least one of an electronic control circuit, an electric power source and a light source. In this way, the injection device may be equipped at least with a limited functionality, thus enabling at least a limited stand-alone operation of the injection device, e.g. when the auxiliary electronic device should not be available or connected to the injection device.

In another example the injection device comprises a medicament reservoir at least partially filled with an injectable medicament. The medicament reservoir may comprise a vitreous barrel having a pierceable seal at a distal end and being sealed by a displaceable bung towards a proximal end.

In another aspect the disclosure relates to an auxiliary electronic device configured for coupling to an injection device as described above. The auxiliary electronic device comprises a housing, a user interface, a processor and a second interface that is configured to connect to the first interface of the injection device. Here, the processor is configured to control at least the electric propulsion of the injection device when the second interface and the first interface are interconnected. The auxiliary electronic device may be thus configured to control operation of the electric propulsion and to control operation of the injection device. Via the user interface the auxiliary electronic device provides an interaction with a user. For operating and for controlling of an injection procedure the user may exclusively communicate or operate with the user interface of the auxiliary electronic device. User commands entered into the user interface of the auxiliary electronic device are processed by the processor of the auxiliary electronic device and are further used to generate respective electric control signals transmitted to the electric propulsion of the injection device via the connected first and second interfaces.

In this way the auxiliary electronic device serves and provides a remote control of the injection device. In some examples the injection device by itself is inoperable. It requires a coupling to the auxiliary electronic device in order to operate or to control the electric propulsion of its drive mechanism.

According to another example the second interface of the auxiliary electronic device comprises a second electric power connector. Furthermore the auxiliary electronic device comprises an electric energy source connected to the second electric power connector. In this way and when appropriately connected to the injection device electric power or electric energy provided by the electric energy source of the auxiliary electronic device can be transferred to the injection device via the electric power connection established by the mutual interconnection of first and second electric power connectors. Typically, the second electric power connector is arranged on or in the second interface in such a way that upon establishing a connection between the first and the second interface also the first power connector is connected to the second power connector.

When establishing a connection between the first and the second interfaces the first electric power connector is connected to the electric energy source of the auxiliary electronic device via the mutually connected first and second electric power connectors. In this way the injection device may be void of an own electric power source or electric energy source. In examples wherein the injection device comprises an own electric power source it may comprise a rechargeable battery that is rechargeable by the electric power source of the auxiliary electronic device as the first and the second electric power connectors are interconnected.

In a further example the second interface comprises a second data connector connected to the processor of the auxiliary electronic device. The second data connector is configured to establish a data connection with the first data connector of the injection device. Typically, the second data connector is located on or in the second interface in such a way, that first and second data connectors mutually interconnect when the first and the second interfaces are interconnected. In this way and upon establishing a connection of the first and the second interfaces also the first and the second data connectors are mutually interconnected and there is established a data connection between the injection device and the auxiliary electronic device.

Via the data connection the processor of the auxiliary electronic device can be electrically connected to the electric propulsion of the drive mechanism of the injection device. In this way the processor of the auxiliary electronic device becomes enabled to control operation of the electric propulsion. Here, the injection device may be void of an own electronic control circuit or of an own processor. In some examples the injection device may comprise an own electronic control circuit that is connectable via the data connection to the processor of the auxiliary electronic device. In this way, the data connection may be of bi-directional type. It may transmit electronic control signals from the processor of the auxiliary electronic device to the electronic control circuit of the injection device. Likewise, electronic data or electronically stored information provided by the electronic control circuit of the injection device can be transferred and transmitted via the data connection to the processor of the auxiliary electronic device.

When the injection device is provided with an own electronic control circuit it may be configured to perform or to conduct at least a limited number of injection procedures in a stand-alone mode, i.e. without an interconnection to the auxiliary electronic device. When appropriately connected with the auxiliary electronic device injection-related data collected and stored in the electronic control circuit of the injection device can be transferred via the data connection to the processor of the auxiliary electronic device for further processing or for reporting and transmission to further electronic devices, e.g. to a computer of a physician in order to control the patient's compliance to a prescribed medication schedule.

According to another example the auxiliary electronic device comprises a second mechanical connector configured to establish mechanical connection with a first mechanical connector of the injection device. The second mechanical connector may comprise at least one of a male or female connector complementary or correspondingly-shaped to a female or male first mechanical connector of the injection device. The mutually corresponding first and second mechanical connectors of the injection device and of the auxiliary electronic device enable a dedicated, well-defined, failure safe and releasable mutual mechanical interconnection of the injection device and the auxiliary electronic device. The first and second mechanical connectors may comprise a pair of mutually corresponding plugs and sockets. For instance, the first mechanical connector may comprise a mechanical plug to be received in a female socket of the auxiliary electronic device.

The first and second mechanical connectors may coincide or may be integrated into respective first and second interfaces of the injection device and of the auxiliary electronic device. For instance, the first mechanical connector may coincide or may be integrated into the first interface. The second mechanical connector may coincide or may be integrated into the second interface. Upon establishing a connection of first and second interfaces the injection device and the auxiliary electronic device may be also mechanically interconnected. Accordingly, upon establishing a mechanical connection between the injection device and the auxiliary electronic device by means of first and second mutually corresponding mechanical connectors the first and the second interfaces of the injection device and of the auxiliary electronic device can be mutually connected.

In some examples the first interface and/or the second interface may be located offset from at least one of the first and the second mechanical connectors. It is conceivable that the first and the second interfaces are exclusively configured to provide at least one of an electric power connection, a data connection or an optical coupling without a mechanical connection between the injection device and the auxiliary electronic device.

In some examples it is conceivable, that the injection device and the auxiliary electronic device are interconnected by a cable or wirelessly while they remain mechanically unconnected or uncoupled. This may provide a rather universal mechanical arrangement of the injection device and the auxiliary electronic device. Hence, for conducting a dose expelling procedure it may not be necessary to mechanically connect the injection device to the auxiliary electronic device. For instance, the auxiliary electronic device may be placed on a table while it is interconnected with the injection device through a cable.

According to another example the auxiliary electronic device comprises a second optical interface configured to establish a light transmitting optical coupling with a first optical interface of the injection device. Typically, the second optical interface comprises at least a light source. Via the optical coupling an optical signal generated by the second optical interface can be transferred to the injection device. In this way, dedicated portions of the injection device can be illuminated by a light source of the auxiliary electronic device. The injection device may be void of an own light source.

The first and second optical interfaces may further allow and support a visual inspection of the medicament located inside the medicament reservoir. For this the second optical interface may comprise a camera configured to receive light reflected or transmitted through the medicament reservoir and being indicative of the integrity of the medicament. For instance, the second optical interface may comprise a light source and a camera configured to measure an optical transmission coefficient of the medicament located inside the medicament reservoir.

In another example the auxiliary electronic device is a portable electronic device. Insofar the auxiliary electronic device is configured as a portable electronic device or as a mobile electronic device. The portable electronic device is configured as a smartphone, as a smartwatch or as a tablet computer. Insofar, existing portable electronic devices, such as a smartphone, a smartwatch or as a tablet computer can serve as an auxiliary electronic device for an injection device.

Existing auxiliary electronic devices, such as smartphones, smartwatches or tablet computers may be configured to act and to behave as an auxiliary electronic device which is enabled to control at least an electric propulsion, hence an electric drive of an injection device. Widely available portable electronic devices, such as smartphones, smartwatches or tablet computers may only have to be equipped with a suitable software or software application, i.e. with an app that enables the respective portable electronic device to communicate with the injection device in such a way that the portable electronic device controls at least the electric propulsion of the injection device.

The second interface of the auxiliary device may comprise a standardized interface following a predefined standard widely used for portable electronic devices. Insofar, the second interface may comprise e.g. a Universal Series Bus (USB) interface, a mini-USB or micro-USB interface with a respective connector. The first interface may comprise a correspondingly or complementary shaped connector. Implementing the first and/or the second interface of the injection device and of the auxiliary electronic device in accordance to a predefined communication standard is beneficial in that existing auxiliary electronic devices, such as smartphones, smartwatches or tablet computers do not require any hardware modification in order to become an auxiliary electronic device configured for interaction with an injection device as described above.

For instance, a large variety of existing portable electronic devices may simply require a software update or installation of a particular software application in order to provide a control of the electric propulsion of the injection device. In this way the injection device may provide a high degree of compatibility with numerous existing portable electronic devices, such as smartphones, smartwatches or tablet computers. The electronic components, in particular the computational power, a user interface and/or an electric power source of a portable electronic device becomes available to the injection device. The injection device may be hence void of at least one of an electronic control circuit, an electric power source and a light source.

An existing user interface of a portable electronic device can be used to communicate with the injection device. The injection device may become software controlled through the software of the auxiliary device. This enables the implementation of numerous programmable functions implemented and provided by the portable electronic device. Individual device settings or user preferences may be provided by the portable electronic device. The portable electronic device may be individually programmed or may be individually configured to provide a rather intuitive operation and handling of the injection device and/or in order to provide a rather intuitive and self-explaining user feedback or user guidance before, during and after the injection procedure.

According to a further example, the second optical interface comprises at least one of a display, a light source and a camera. Here, a display of a smartphone, of a smartwatch or of a tablet computer may provide a visual and tactile user interface for the injection device. The display may comprise a touch sensitive display. The display of the portable electronic device may be further used as a light source to illuminate at least a portion of the injection device when mechanically connected to the auxiliary electronic device. In this way, the display of the auxiliary electronic device may provide a visual user feedback that is transmitted through the injection device.

The second optical interface may also comprise a dedicated and separate light source located outside the display of the auxiliary electronic device, e.g. outside of a display of the portable electronic device. The light source may be implemented as a flashlight or as an auxiliary light, e.g. implemented as a light emitting diode on a backside of a housing of a portable electronic device. The backside is typically located opposite to a front side of the portable electronic device, wherein the front side is provided with a graphical user interface, e.g. with a touch sensitive two-dimensional display. The second optical interface may further comprise a camera. For this a camera of an existing portable electronic device, such as the camera of a smartphones, of a smartwatches or of a tablet computer can be used. By means of the camera an optical and visual inspection of, e.g. the medicament contained inside the medicament reservoir can be conducted.

In some examples the auxiliary electronic device is configured for attachment of an injection device to a front side of the auxiliary electronic device. In other embodiments the auxiliary electronic device is configured to attach the injection device to a backside of the auxiliary electronic device. In further examples the auxiliary electronic device may be configured for a variable connection of the injection device. Hence, the auxiliary electronic device may be configured for selectively attaching the injection device either to a front side of the auxiliary electronic device or to a backside of the auxiliary electronic device.

In another aspect the disclosure further relates to an injection system comprising an injection device as described above and further comprising an auxiliary electronic device as described above. Insofar all embodiments, examples, benefits and effects described above in connection with the injection device and/or in connection with the auxiliary electronic device are equally valid for the injection system.

According to a further aspect the disclosure relates to a computer program comprising computer-readable instructions which, when executed by a processor of an auxiliary electronic device as described above, causes the auxiliary electronic device to control an electric propulsion or an electric drive of an injection device as described above when the injection device is coupled, i.e. connected to the auxiliary electronic device. Typically, the injection device, the auxiliary device and the injection system as well as the computer program are configured to provide extended and improved control features on a user interface of the auxiliary electronic device. Typically, on the user interface of the auxiliary electronic device, e.g. on a touch sensitive display of a portable electronic device there are provided certain buttons or actuators that can be manually operated by a user of the injection device, or injection system in order to trigger and/or to control the injection procedure. The coupling and connection between the injection device and the auxiliary electronic device provide software implemented control features on the user interface of the auxiliary electronic device that enable a user to control, e.g. to trigger an injection device process.

All aforementioned functions, effects and features described in connection with the injection device, described in connection with the auxiliary electronic device are equally valid for the computer program; and vice versa.

It is further to be noted, that the first interface and the second interface of the injection device and of the auxiliary electronic device, respectively might be configured as wired connections in order to transmit electric power, data and/or optical signals between the auxiliary electronic device and the injection device. However, at least for the data connection it is also conceivable to establish a wireless connection between the auxiliary electronic device and the injection device. Insofar, the first data connector of the injection device may be configured for wireless communication with the second data connector of the auxiliary electronic device. Here, the first and/or second data connectors may be configured to exchange data on the basis of one of a plurality of available wireless data transmission standards, such as Wi-Fi, NFC or RFID.

In other examples it is even conceivable, that the first electric power connector of the injection device and the second electric power connector of the auxiliary electronic device are configured for wireless power transmission, e.g. by an inductive electrical coupling. In a further example a light transmitting optical coupling established by the first optical interface of the injection device and the second optical interface of the auxiliary electronic device may be implemented by an optical fiber interconnecting the first optical interface and the second optical interface. Insofar and in order to establish at least one or several of an electric power connection, a data connection and an optical coupling between the injection device and the auxiliary electronic device a mechanical interconnection of the injection device and the auxiliary electronic device may not be mandatory or necessary.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, numerous examples of the container and of an injection device will be described in greater detail by making reference to the drawings, in which.

DETAILED DESCRIPTION

Figure 1:
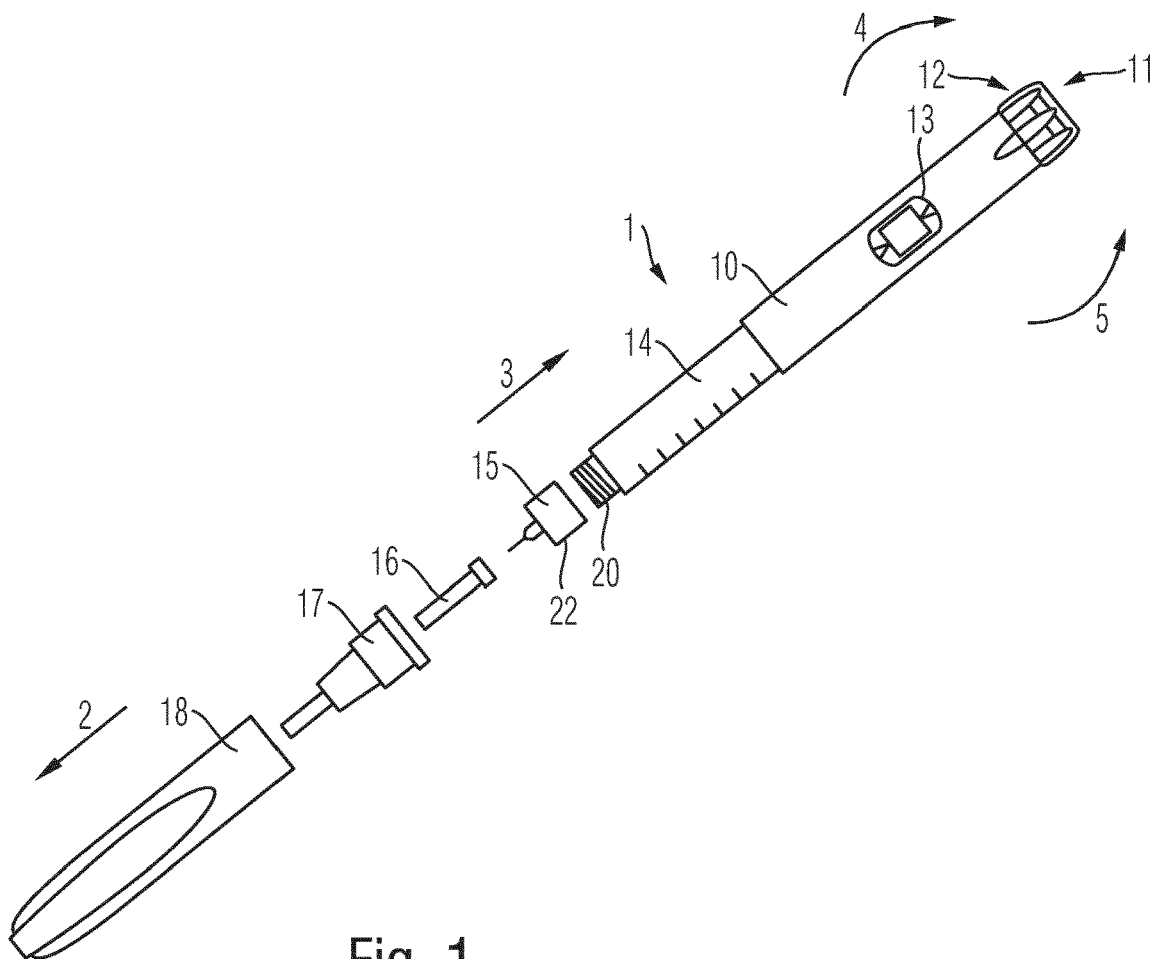
FIG. 1 shows a schematic illustration of a pen-type injection device.
Figure 2:
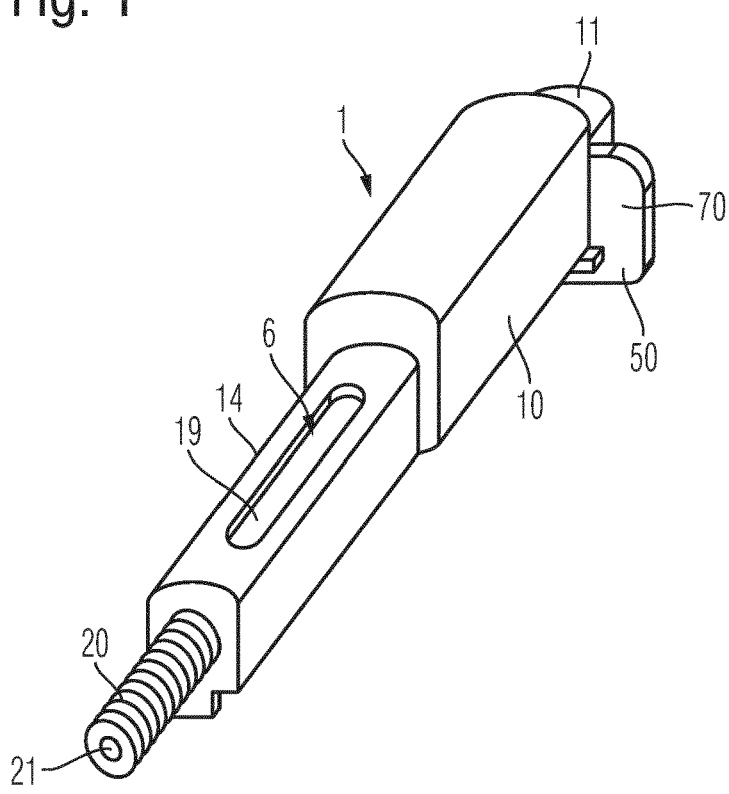
FIG. 2 is a perspective view of an injection device provided with a first interface.
Figure 5:
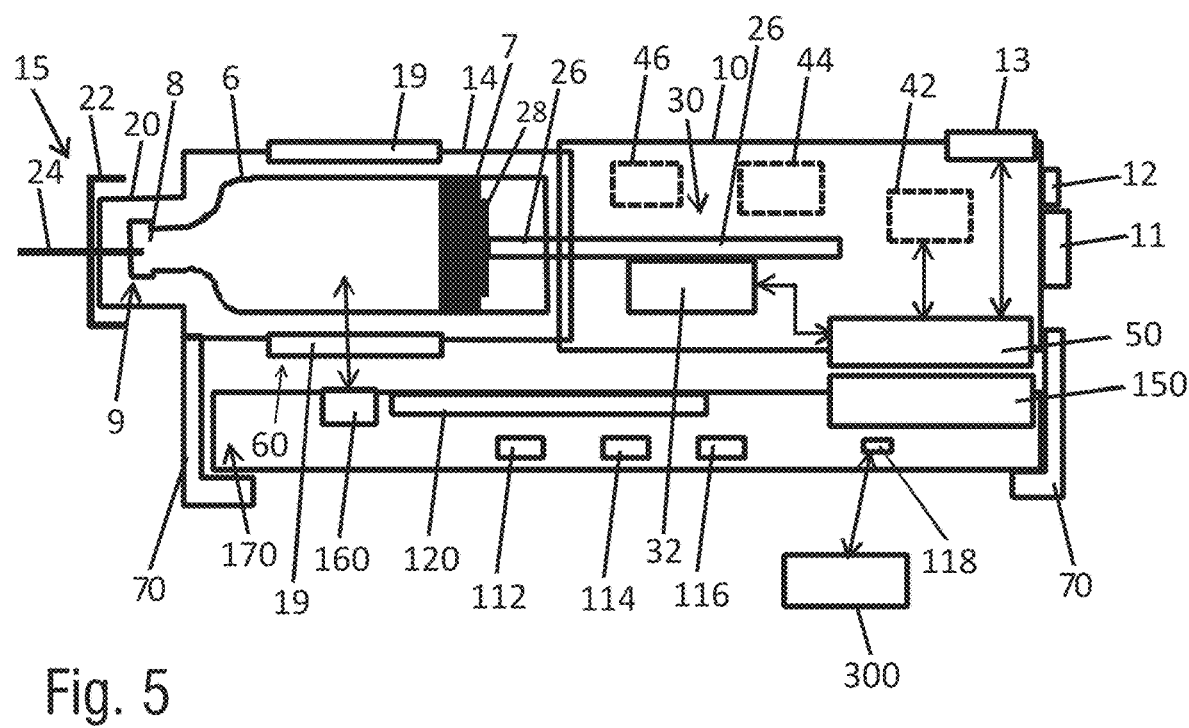
FIG. 5 is a schematic block diagram of various components of the injection system of FIG. 3 or 4.

The injection device 1 as shown in FIGS. 1 and 2 is a pre-filled disposable injection device that comprises a housing 10 to which a needle assembly 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 30 as indicated in FIG. 5. The injection device 1 may further comprise a distal housing component denoted as drug container holder 14. The drug container holder 14 may be permanently or releasably connected to the main housing 10. The drug container holder 14 is typically configured to accommodate a drug container 6 that is filled with a liquid medicament. The drug container 6 may comprise a cartridge that is sealed towards a distal end by a pierceable seal, such as a septum.

The injection device 1 as illustrated in FIGS. 2-5 may be slightly modified to the injection device 1 as illustrated in FIG. 1. The injection device 1 according to FIGS. 2-5 may be void of a dosage window 13. It may be also void of a dose dial 12 and/or void of a dose trigger 11. Optionally and as illustrated in FIG. 5, the injection device 1 may comprise an own dosage window 13, e.g. in form of an electronic display. The injection device 1 as illustrated in FIGS. 2-5 may also comprise a trigger 11 or a dose dial 12 for a manual and stand-alone operation and/or control of the injection device 1 if required.

As illustrated in FIG. 5 the injection device 1 comprises a housing 10 and a container 6 filled with a liquid medicament. The container 6 provides a medicament reservoir. It may comprise a substantially tubular-shaped barrel or bottle filled with the liquid medicament. Towards a proximal direction 3 the medicament reservoir 6 may be closed by a displaceable bung 7 or stopper. The bung 7 may be in mechanical contact with a piston rod 26 configured for a stepwise distally directed displacement in order to urge the bung 7 further in distal direction and hence towards the outlet 8 of the medicament reservoir 6. At or near the outlet 8 the medicament reservoir 6 comprises a pierceable membrane 9. The needle assembly 15 comprises a threaded needle hub 22 configured for a screwed connection with the threaded socket 20 provided on a distal end of the drug container holder 14. As illustrated in FIG. 2, the very distal end of the drug container holder 14 comprises a through opening 21 to receive a proximal tipped section of the injection needle 24. In particular, the injection device needle 24 of the needle assembly 15 intersects the needle hub 22 and comprises a double-tipped cannula.

The injection device 1 comprises a drive mechanism 30. The drive mechanism 30 comprises an electric propulsion 32, e.g. in form of an electric drive or electric motor. The electric propulsion is mechanically engaged with the piston rod 26 in order to urge the piston rod in distal direction 2 for expelling of a dose of the medicament from the medicament reservoir 6. As indicated in FIG. 5, the distal end of the piston rod 26 comprises a pressure piece 28 having a radially widened structure compared to the elongated piston rod 26. The pressure piece 28 will get in direct mechanical contact with a proximal face of the bung 7 in order to displace the bung 7 relative to the sidewall of the medicament reservoir 6. The piston rod 26 may comprise a threaded rod that is in threaded engagement with the housing 10. The electric propulsion 32 may be configured to induce or to apply a driving torque to the piston rod 26. Optionally, there is provided a gear or gearbox by way of which the electric propulsion 32 is mechanically connected to the piston rod 26.

In other examples the injection device 1 is equipped with a flexible reservoir 6, e.g. in form of a flexible bag connected to a suction pump. Here, the drive mechanism 30 of the injection device 1 comprises an electrically operated suction pump rather than an electric drive. The drive mechanism 30 and the suction pump are configured to withdraw a predefined dose of the medicament from the flexible reservoir. The injection device may be even configured as an infusion device configured to expel or to dispense an amount of the medicament at a predefined or at a user-definable rate over time.

Figure 3:
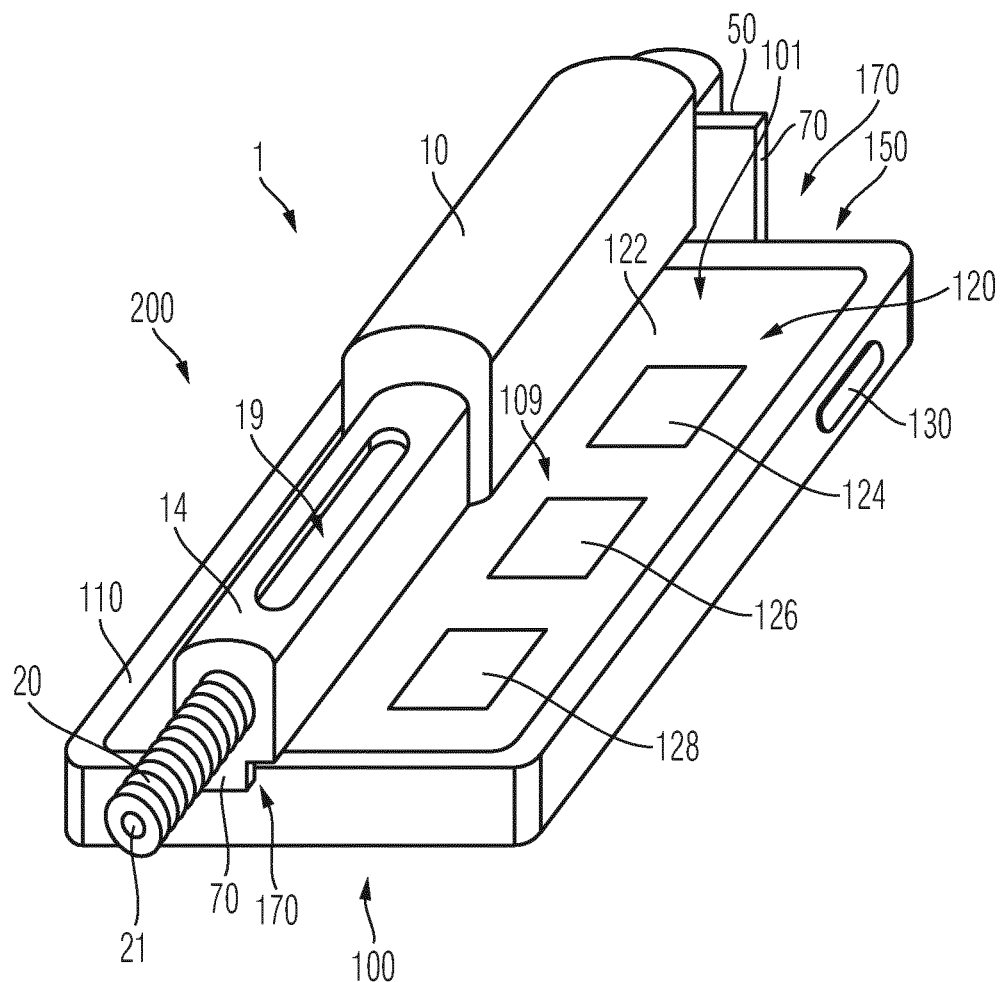
FIG. 3 shows an injection system comprising the injection device of FIG. 2 connected to an auxiliary electronic device.
Figure 4:
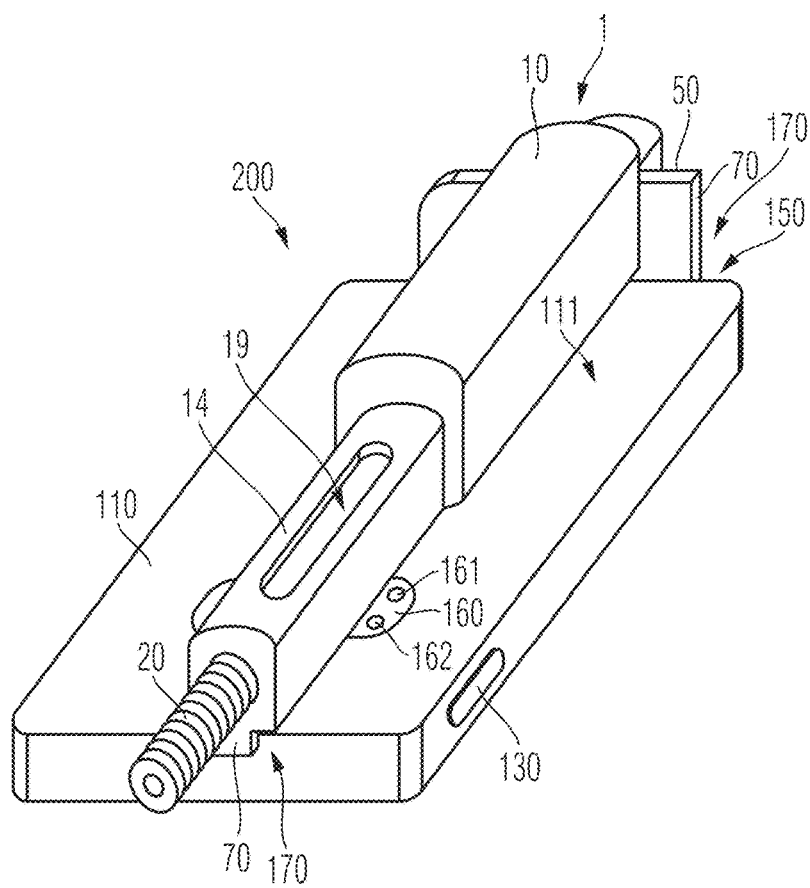
FIG. 4 shows another configuration of the injection system according to FIG. 3.
Figure 9:
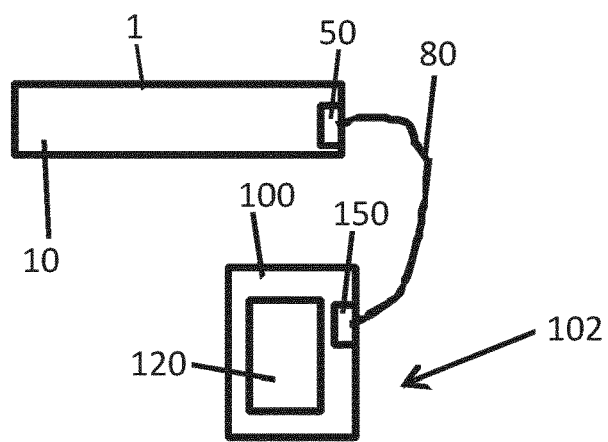
FIG. 9 is a schematic illustration of a wired connection or coupling between the injection device and the auxiliary electronic device.

The injection device 1 further comprises a first interface 50 that is directly or indirectly connected to the electric propulsion 32. The first interface is configured for connection to a second interface 150 of an auxiliary electronic device 100 as illustrated in FIGS. 3-5. The auxiliary electronic device 100 is currently illustrated as a portable electronic device configured as a smartphone 101. The auxiliary electronic device may be alternatively embodied as a smartwatch or as a portable tablet computer 102 as indicated in FIG. 9. By means of the mutually corresponding interfaces 50, 150 the auxiliary electronic device becomes enabled to control the electric propulsion 32 of the injection device 1.

The assembly of the auxiliary electronic device 100 and the injection device 1 form or constitute an injection system 200 as illustrated in FIGS. 3 and 4.

Figure 6:
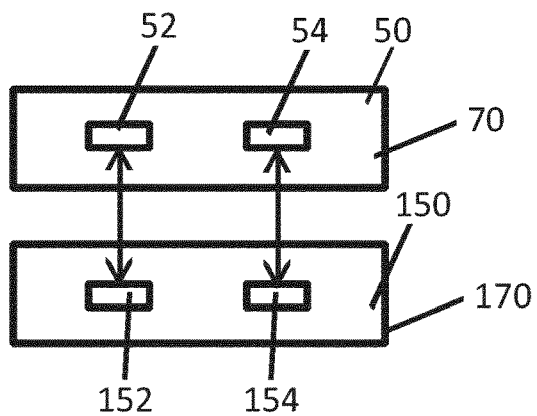
FIG. 6 is a block diagram of first and second interfaces of the injection device and of the auxiliary electronic device.

As further indicated in FIG. 6 the first interface 50 comprises a first electric power connector 52 that is configured to establish an electric power connection with a correspondingly- or complementary-shaped second electric power connector 152 of the second interface 150. In this way and upon interconnecting the first interface 50 with the second interface 152 there is established an electric power connection between the injection device 1 and the auxiliary electronic device 100.

As further illustrated in FIG. 6 the first interface 50 may also comprise a first data connector 54 configured to establish a data connection with a second data connector 154 that belongs to the second interface 150. In this way and upon establishing a connection between the first interface 50 and the second interface 150 also a data connection between the first data connector 54 and the second data connector 154 can be established. In this way the injection device 1 and the auxiliary electronic device 100 may exchange electric power as well as electronic data. When the first and second interfaces 50, 150 comprise or form an electric power connection the injection device 1 may be void of an own electric power source 44 as indicated with dashed lines in FIG. 5.

In a further example the injection device 1 may be further void of an electronic control circuit 42. Such an electronic control circuit 42 may be provided only optionally to the injection device 1 in order to equip the injection device 1 at least with a basic or fallback functionality to operate the electric propulsion 32 and/or the electrically implemented drive mechanism 30 in circumstances or cases where an interconnection with the auxiliary electronic device 100 should not be available. Generally, the injection device 1 may be void of an own electronic control circuit 42. This is particularly the case when the first and second interfaces 50, 150 comprise mutually corresponding first and second data connectors 54, 154.

By way of the data connection established by first and second data connectors 54, 154 medication related or injection related information can be exchanged between the injection device 1 and the auxiliary electronic device 100. For instance, via the data connection a dosage size and a point of time where a recent or a series of recent doses have been expelled can be transmitted to the auxiliary electronic device.

As indicated further in FIG. 5 the injection device may optionally comprise a first optical interface 60 that is configured to establish a light transmitting optical coupling with a second optical interface 160 of the auxiliary electronic device 100. In one implementation the first optical interface 60 may comprise a window 19 in the housing 10 or in the drug container holder 14 of the injection device 1. The window 19 may provide visual inspection of the medicament located in the medicament reservoir 6. A sidewall or at least a portion of the sidewall of the medicament reservoir 6 may be transparent or translucent. The second optical interface 160 typically comprises at least one of a light source 161 and a camera 162. The second optical interface 160 may be provided on a front side 109 of a housing 110 of the auxiliary electronic device 100 or on a backside 111 of the auxiliary electronic device 100 as indicated in FIG. 4.

When the second optical interface 160 is provided on a backside 111 of the auxiliary electronic device 100 the second optical interface 160 may comprise both, a light source 161, such as a flashlight and a camera 162. The light source 161 and the camera 162 or a respective light detector may be configured to emit a light beam or to emit light pulses over the optical coupling into the first optical interface 60, hence through the window 19 to illuminate the medicament located inside the medicament reservoir (6).

Light reflections and reflected light returning to the second optical interface 160 and captured by the camera 162 the auxiliary electronic device, in particular a processor 114 thereof, may be configured to determine whether the medicament still fulfills optical inspection criteria. For instance, if the intensity or a wavelength of light detected by the detector or camera 162 should be below or above a given threshold this might be an indication, that the medicament should be no longer used. Then, and upon detecting such an inadmissible optical property of the medicament, the processor 114 of the auxiliary electronic device may be configured to produce or to generate an alert on a user interface 120, typically provided on a front side 109 of the auxiliary electronic device 100.

The user interface 120 of the auxiliary electronic device 100 may provide numerous visual sections or elements. In particular, the user interface 120 comprises a touch sensitive display 122 on the front side 109 of the auxiliary electronic device 100. On the user interface 120 or on the display 122 numerous dedicated sections or portions may be visually illustrated to the user of the auxiliary electronic device. For instance, there may be provided a control element 124, a feedback element 126 and an instruction element 128. The shape, location and appearance of these various graphically represented elements 124, 126, 128 may be individually configured and may be subject to dynamic changes both in terms of their geometry, brightness, color or other optical characteristics.

The instruction element 128 may be configured to provide a visual guidance for the user about various handling steps with regard to the injection device. For instance, the instruction element 128 may contain readable instructions or pictorial instructions that are intuitively understandable by a user for a proper handling of the injection device 1. The instruction element 128 may be configured to indicate to a user, that at least one of the protective cap 18, the outer needle cap 17 or the inner needle cap 16 should be removed. The instruction element 128 may be further indicative to activate a dose setting procedure, hence to select or to set a dose of predetermined size. The instruction element 128 may inform the user about the size of a dose to be set or to be dispensed.

The control element 124 may be of touch sensitive type. Upon touching or activating the control element 124, e.g. by a thumb or some other finger of the user the processor 114 of the auxiliary electronic device 100 may be triggered to control the electric propulsion 32 for dispensing of a predefined amount of the medicament from the medicament reservoir 6. In addition, the auxiliary electronic device 100 may comprise a mechanical actuation element 130, e.g.

located on an outer frame of the housing 110 of the auxiliary electronic device 100. The actuation element 130 may be depressible in order to trigger an injection procedure or to trigger the electric propulsion 32. There may be further provided a feedback element 126 indicating to the user that, e.g. an injection process is due, that an injection process is currently in progress or that an injection process has terminated.

The second optical interface 160 may geometrically overlap with the drug container holder 14 or with some other part of the housing 10 of the injection device. Since the drug container holder 14 comprises at least one or several windows 19 the second optical interface 160 may be configured to illuminate the drug container holder through the windows 19 thereof. Here, the windows 19 of the drug container holder 14 may form the first optical interface. In this way, a portion of the display 122 that overlaps with the window 19 of the drug container holder may be used to illuminate the drug container holder. The second optical interface 160 may be configured to transmit optical signals of different wavelength to the first optical interface and hence to or through the window 19 of the drug container holder 14.

In this way, different modes or states of the injection device or of an injection process can be color encoded. For instance, during an injection procedure the second optical interface may emit optical signals in the red spectral range. After termination of a successful injection procedure the second optical interface may be configured to transmit optical signals in another spectral range to the first optical interface, e.g. in the green spectral range. In this way, the drug container holder 14 or some other portion of the injection device 1 may be illuminated in a red or green color. For this and due to the optical coupling the injection device 1 does not require an own light source. However, such an own light source 46 may be present in the injection device. This enables operation of the injection device at least in a fallback mode so that the injection device 1 provides at least a minimum of user feedback when operated in a stand-alone mode, e.g. without an interconnection with the auxiliary electronic device 100.

The auxiliary electronic device 100 typically comprises an electric power source 112, such as a rechargeable battery. Upon establishing a connection between the auxiliary electronic device 100 and the injection device 1 electric power for driving of the electric propulsion 32 can be exclusively or at least partially provided by the electric power source 112 of the auxiliary electronic device 100. Insofar, the injection device 1 may be void of an own electric power source 44. In some examples such an electric power source 44 may be present in the injection device, in order to enable at least a fallback or emergency operation of the injection device if a coupling to the auxiliary electronic device 100 should not be possible or available.

Typically, the auxiliary electronic device 100 comprises a memory 116 connected to the processor 114. In the memory 116 injection related information obtained through a data connection between the first and the second data connectors 54, 154 can be stored. Typically, the auxiliary electronic device 100 also comprises a communication interface 118. The communication interface may be configured for a wired or wireless connection to a further external electronic device, such as another portable or stationary electronic device, such as another smartphone, another smartwatch, another tablet computer or another personal computer.

The communication interface 118 may coincide with the second interface 150. Moreover, the second interface 150 may provide a communication interface 118 for connecting the auxiliary electronic device 100 to at least one further portable electronic device 300. In this way, data stored in the memory 116 and obtained via the connection of the interfaces 50, 150 can be further transmitted to other electronic devices 300 that may be implemented as portable or stationary electronic devices.

The communication interface 118 may be configured to communicate with the at least further electronic device 300 via a network, such as the internet.

As indicated further in FIG. 5 the injection device comprises a first mechanical connector 70 that is configured to establish a mechanical connection with the auxiliary electronic device 100. As indicated in FIG. 5, there may be provided numerous mechanical connectors 70 on the housing 10 of the injection device 1. For instance, one mechanical connector may be provided at a proximal end of the housing 10 and another mechanical connector 70 may be provided at a distal end of the injection device. This allows for an at least twofold mechanical connection between the injection device 1 and the auxiliary electronic device 100.

The first mechanical connector may be configured to establish at least one of a form fit or a force-type connection, e.g. a friction fit with the housing 110 of the auxiliary electronic device 100. The first mechanical connector 70 may comprise a clamp or a clip configured to establish a clamped or a clipped connection with the housing 110 of the auxiliary electronic device 100. The first mechanical connector may further comprise at least one of a male or female mechanical connector correspondingly-shaped to a female or male counter connector of the auxiliary electronic device 100. For instance, the first mechanical connector 70 may comprise a plug complementary-shaped to a socket of the auxiliary electronic device. It is of particular benefit, when the first mechanical connector coincides with the first interface or a portion thereof. The first mechanical connector may be integrated into the first interface.

Figure 7:
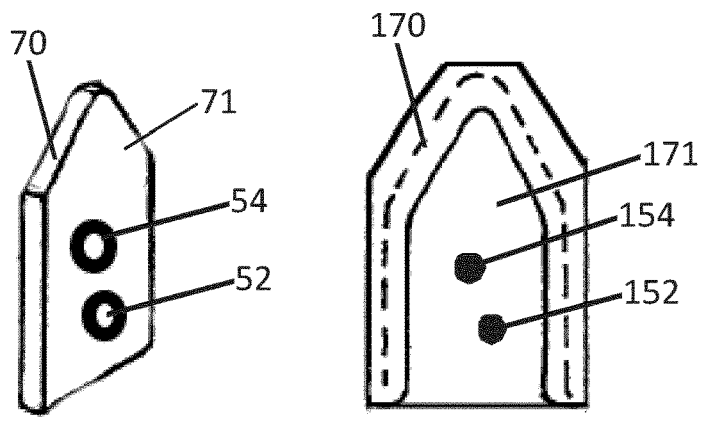
FIG. 7 shows a schematic implementation of a combined mechanical and electric interface.

A correspondingly-shaped mechanical connector of the auxiliary electronic device may coincide with the second interface or may be integrated into the second interface. Hence, the auxiliary electronic device may optionally comprise a second mechanical connector 170 as for instance indicated in FIG. 7. The second mechanical connector 170 may be shaped and configured to receive the first mechanical connector 70 provided on an outside surface of the injection device 1. The second mechanical connector 170 may comprise a contact surface 171 that is configured to get in abutment with a counterpart contact surface 71 of the first mechanical connector 70. On the contact surface 71 there is provided for instance the first electric power connector 51 and the first data connector 54. On the counterpart contact surface 171 of the second mechanical connector 170 there is provided the second electric power connector 152 and the second data connector 154.

Upon establishing a mechanical connection on the basis of the mutually corresponding first and second mechanical connectors 70, 170, e.g. by sliding the first mechanical connector 70 into a receptacle 172 of the second mechanical connector 170 and upon reaching of a final assembly configuration, in which the side edge 72 of the first mechanical connector 70 is enclosed by the receptacle 172 an electric power connection is formed between the first and second electric power connectors 52, 152. In addition to that, a data connection can be established between the first and second data connectors 54, 154, respectively.

Figure 8:
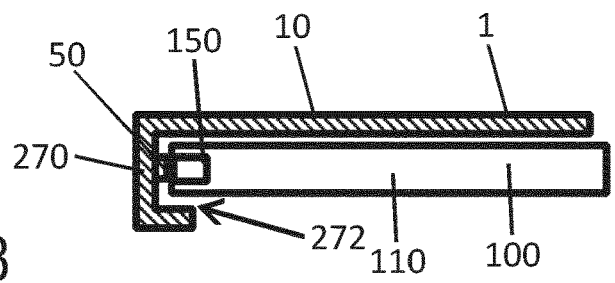
FIG. 8 is a cross-section through a mechanical interface between the injection device and the auxiliary electronic device.

In FIG. 8 a further example of a first mechanical connector 270 is illustrated. Here, the first mechanical connector 270 comprises or forms a receptacle 272 to receive at least a portion of the housing 110 of the auxiliary electronic device 100. For instance, receptacle 272 may form a hollow shaft configured to slidingly receive a longitudinal end of the housing 110 of the auxiliary electronic device 100. The respective longitudinal end of the housing 110 of the auxiliary electronic device 100 that is receivable in the receptacle 272 may be provided with the second interface 250.

Upon reaching a final assembly configuration, i.e. when inserting the auxiliary electronic device 100 into the receptacle 272 of the injection device 1 the first interface 50 is connected with the second interface 150 and no further manual interconnection of first and second interfaces 50, 150 has to be conducted. In this way and as a mechanical interconnection of the injection device 1 and the auxiliary electronic device 100 is established, the two devices, 1, 100 are automatically connected in terms of at least one of an electric power connection, a data connection and an optical coupling.

In the example of FIG. 9 it is further illustrated, that the first and the second interface 50, 150 may be connected by a wire or cable 80. In this way, the first interface 50 and the second interface 150 can be interconnected independent of a mechanical connection of the housing 10 of the injection device with the housing 110 of the auxiliary electronic device 100.

LIST OF REFERENCE NUMBERS 1 injection device
2 distal direction
3 proximal direction
4 dose incrementing direction
5 dose decrementing direction
6 drug container
7 bung
8 outlet
9 membrane
10 housing
11 trigger
12 dose dial
13 dosage window
14 drug container holder
15 needle assembly
16 inner needle cap
17 outer needle cap
18 protective cap
19 window
20 threaded socket
21 through opening
22 needle hub
24 injection needle
26 piston rod
28 pressure piece
30 drive mechanism
32 electric propulsion
42 electronic control circuit
44 electric power source
46 light source
50 interface
52 electric power connector
54 data connector
60 optical interface
70 mechanical connector
71 contact surface
80 cable
100 auxiliary electronic device
101 smartphone 102 tablet computer
109 front side
110 housing
111 backside
112 electric power source
114 processor
116 memory
118 communication interface
120 user interface
122 display
124 control element
126 feedback element
128 instruction element
130 actuation element
150 interface
152 electric power connector
154 data connector
160 optical interface
161 light source
162 camera
170 mechanical connector
171 contact surface
172 receptacle
200 injection system
270 mechanical connector
272 receptacle
300 electronic device

The invention claimed is:

1. An injection device configured for expelling of a dose of a medicament, the injection device comprising:
a housing configured to accommodate a medicament reservoir;
a drive mechanism comprising an electric propulsion device configured to mechanically interact with the medicament reservoir and configured to withdraw or to expel an amount of the medicament from the medicament reservoir; and
a first interface directly or indirectly connected to the electric propulsion device and configured to connect to a second interface of an auxiliary electronic device,
wherein the electric propulsion device is controllable by the auxiliary electronic device when the first interface and the second interface are interconnected
wherein the first interface comprises a first electric power connector configured to establish an electric power connection with a second electric power connector of the second interface to power the electric propulsion device.

2. The injection device according to claim 1, wherein the first interface comprises a first data connector configured to establish a data connection with a second data connector of the second interface.

3. The injection device according to claim 1, further comprising a first mechanical connector configured to establish a mechanical connection with the auxiliary electronic device.

4. The injection device according to claim 1, further comprising a first optical interface configured to establish a light transmitting optical coupling with a second optical interface of the auxiliary electronic device.

5. The injection device according to claim 1, wherein the injection device is void of at least one of an electronic control circuit, an electric power source, or a light source.

6. The injection device according to claim 1, wherein the drive mechanism includes an electric motor.

7. The injection device according to claim 1, wherein electric power is transferable from the auxiliary electronic device to the injection device when the first electric power connector is connected to the second electric power connector.

8. The injection device according to claim 1, wherein the injection device is void of an electric power source, and the electric propulsion device receives electric power from the auxiliary electronic device.

9. A medical system comprising:
an injection device; and
an auxiliary electronic device configured for coupling to the injection device,
wherein the injection device comprises:
a first housing configured to accommodate a medicament reservoir;
a drive mechanism comprising an electric propulsion device configured to mechanically interact with the medicament reservoir and configured to withdraw or to expel an amount of medicament from the medicament reservoir, and
a first interface directly or indirectly connected to the electric propulsion device, the first interface comprising a first electric power connector, and
wherein the auxiliary electronic device comprises:
a second housing,
a user interface,
a processor, and
a second interface configured to connect to the first interface of the injection device, the second interface comprising a second electric power connector operable to establish an electric power connection with the first electric power connector to power the electric propulsion device,
wherein the processor of the auxiliary electronic device is configured to control the electric propulsion device of the injection device when the second interface of the auxiliary electronic device and the first interface of the injection device are interconnected via the first and the second power connectors.

10. The medical system according to claim 9, wherein the auxiliary electronic device comprises an electric power source connected to the second electric power connector.

11. The medical system according to claim 9, wherein the second interface comprises a data connector connected to the processor.

12. The medical system according to claim 11, wherein the first interface comprises a data connector configured to establish a data connection with the data connector of the second interface.

13. The medical system according to claim 9, wherein the auxiliary electronic device further comprises a mechanical connector configured to establish a mechanical connection with a mechanical connector of the injection device.

14. The medical system according to claim 9, wherein the auxiliary electronic device further comprises an optical interface configured to establish a light transmitting optical coupling with an optical interface of the injection device.

15. The medical system according to claim 14, wherein the optical interface of the auxiliary electronic device comprises at least one of a display, a light source, and a camera.

16. The medical system according to claim 9, wherein the auxiliary electronic device comprises a portable electronic device, the portable electronic device being at least one of a smartphone, a smart watch, and a tablet computer.

17. A non-transitory computer-readable medium storing one or more instructions which, when executed by a processor of an auxiliary electronic device, causes the auxiliary electronic device to control a transfer of electric power from the auxiliary electronic device to an electric propulsion device of an injection device when a first electric power connector of the injection device is electrically connected to a second electric power connector of the electronic auxiliary device.

18. The non-transitory computer-readable medium according to claim 17, wherein the one or more instructions executed by the processor cause the auxiliary electronic device to control dispensing of a medicament from the injection device by controlling an interaction of the electric propulsion device with a medicament reservoir containing the medicament.

19. The non-transitory computer-readable medium according to claim 18, wherein the instructions further cause the auxiliary electronic device to control dispensing of a predefined amount of the medicament.

20. The non-transitory computer-readable medium according to claim 17, wherein the instructions further cause providing a feedback to a user, the feedback indicating that an injection process is currently in progress or has terminated.

\* \* \* \* \*